(12) United States Patent
Pelletier et al.

(10) Patent No.: US 9,683,932 B2
(45) Date of Patent: Jun. 20, 2017

(54) VARIABLE ICE AND METHODS FOR MEASURING SAMPLE PROPERTIES WITH THE SAME

(71) Applicant: Halliburton Energy Services, Inc., Houston, TX (US)

(72) Inventors: Michael T. Pelletier, Houston, TX (US); David L. Perkins, The Woodlands, TX (US); Li Gao, Katy, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 14/904,474

(22) PCT Filed: Sep. 12, 2013

(86) PCT No.: PCT/US2013/059493
§ 371 (c)(1),
(2) Date: Jan. 12, 2016

(87) PCT Pub. No.: WO2015/038131
PCT Pub. Date: Mar. 19, 2015

(65) Prior Publication Data
US 2016/0209323 A1     Jul. 21, 2016

(51) Int. Cl.
*G01N 21/31* (2006.01)
*G01N 21/33* (2006.01)
*G01N 21/35* (2014.01)

(52) U.S. Cl.
CPC .............. *G01N 21/31* (2013.01); *G01N 21/33* (2013.01); *G01N 21/35* (2013.01)

(58) Field of Classification Search
CPC .......... G01N 21/31; G01N 21/33; G01N 21/35
See application file for complete search history.

(56) References Cited

U.S. PATENT DOCUMENTS

| | | | |
|---|---|---|---|
| 5,808,473 A | 9/1998 | Shinagawa et al. |
| 6,211,961 B1 | 4/2001 | Maris |
| 6,281,489 B1 | 8/2001 | Tubel et al. |
| 2003/0173504 A1 | 9/2003 | Cole |
| 2006/0228089 A1 | 10/2006 | Shimokozono et al. |

(Continued)

FOREIGN PATENT DOCUMENTS

WO     WO 2013/089764 A1     6/2013

OTHER PUBLICATIONS

International Preliminary Report on Patentability, May 14, 2015, PCT/US2013/059493, 9 pages, IPEA/US.

(Continued)

*Primary Examiner* — Mark R Gaworecki
(74) *Attorney, Agent, or Firm* — Haynes and Boone, LLP

(57) ABSTRACT

A system and method for measuring properties of a sample utilizing a variable integrated computation element (ICE) formed of one or more layers of film that is physically sensitive to an electrical field or a magnetic field applied through the material. The thickness of a layer, and hence the optical properties of the ICE, can be electrically or magnetically altered to adjust the ICE for a analysis of a particular property of the sample, or to calibrate the ICE or to adjust the ICE to compensate for alterations to the ICE resulting from environmental conditions. The film may be formed of electrostrictive materials, piezoelectric materials, magnetorestrictive materials, and/or piezomagnetic materials.

22 Claims, 8 Drawing Sheets

(56) References Cited

U.S. PATENT DOCUMENTS

2007/0046605 A1    3/2007  Fujimori et al.
2008/0107372 A1    5/2008  Fujimori et al.
2010/0265509 A1   10/2010  Jones et al.
2013/0031964 A1    2/2013  Tunheim et al.

OTHER PUBLICATIONS

International Search Report and The Written Opinion of the International Searching Authority, or the Declaration, Jan. 29, 2014, PCT/US2013/059493, 10 pages, ISA/US.
Yang, et al., "Field-Induced Strain Associated with Polarization Reversal in a Rhombohedral Ferroelectric Ceramic." J. Mater. Res., vol. 18, No. 12, Dec. 2003, pp. 2869-2873.

VARIABLE ICE AND METHODS FOR MEASURING SAMPLE PROPERTIES WITH THE SAME

The present application is a U.S. National Stage patent application of International Patent Application No. PCT/US2013/059493, filed on Sep. 12, 2013, the benefit of which is claimed and the disclosure of which is incorporated herein by reference in its entirety.

BACKGROUND

1. Technical Field

Embodiments disclosed herein relate to the field of integrated computational elements (ICEs) for optical measurements of fluid samples. In particular, embodiments disclosed herein relate to the field of variable ICEs and methods of fabricating the same.

2. Description of Related Art

In the field of hydrocarbon exploration and extraction there is often the need to perform measurements of samples to determine their chemical composition and other measureable fluid properties. In many cases, methods and systems to perform optical measurements use a spectrally resolved optical element to analyze a sample light. Filters and other spectrally resolved optical devices in state-of-the-art technology are passive devices. Thus, state of the art spectrally resolved optical devices and components typically require continuous re-calibration procedures to correct for fabrication errors, and also to correct for expected drifts due to environmental wear. Furthermore, changing environmental conditions, particularly as experienced in downhole hydrocarbon wells, such as temperature, pressure, and humidity adversely affect the performance of a passive spectrally resolved optical element. Typically, a spectrally resolved optical element or filter includes a plurality of thin dielectric layers prone to contraction or expansion, according to different environmental conditions. The problem is exacerbated when the number of thin dielectric layers is large, such as 10, 20, 50, or even more layers.

Another drawback of conventional filters and other spectrally resolved optical devices is manufacturing repeatability. Indeed, under the most stringent manufacturing tolerances, variability exists in results that need to be considered. Variability adjustments include manufacturing a separate adjustment element especially designed for a particular unit, or introducing continuous calibration measurement steps in the measurement protocols. These approaches are either costly from the manufacturing point of view, or unnecessarily complicate measurement procedures, imposing a heavy load in computational resources, especially as can be applied in downhole hydrocarbon wells.

What is needed is a variable spectrally resolved device allowing real-time error adjustment and environmental adjustment, and a method for using the same in sample measurements.

BRIEF DESCRIPTION OF THE DRAWINGS

Wherever possible, the same reference numbers are used throughout the drawings to refer to the same or like elements.

DETAILED DESCRIPTION

Embodiments disclosed herein provide a rugged and compact optical measurement system including an integrated computational element (ICE). State-of-the-art optical measurement techniques in hydrocarbon exploration and extraction typically cover a wide spectral range involved in the measurement, including the ultraviolet (UV, 10 nm-350 nm), the visible (VIS, 350 nm-770 nm) and near infrared (NIR, 770 nm-2500 nm) to the mid-infrared spectral regions and beyond (MIR, 2.5 µm-50 µm). To provide detailed compositional information of a sample, some embodiments may include a plurality of ICEs covering an entire optical spectrum of interest, including the UV, VIS, NIR, and MIR spectral regions.

In some embodiments, a variable ICE is used to correct in real time for fabrication errors or environmental adjustments of the measurement system. Thus, embodiments as disclosed herein significantly reduce the complexity of the system, simplifying alignment of different optical components, boosting reliability of the sensor's mechanical, electrical and electronic components, and reducing the number of moving parts.

Figure 1:
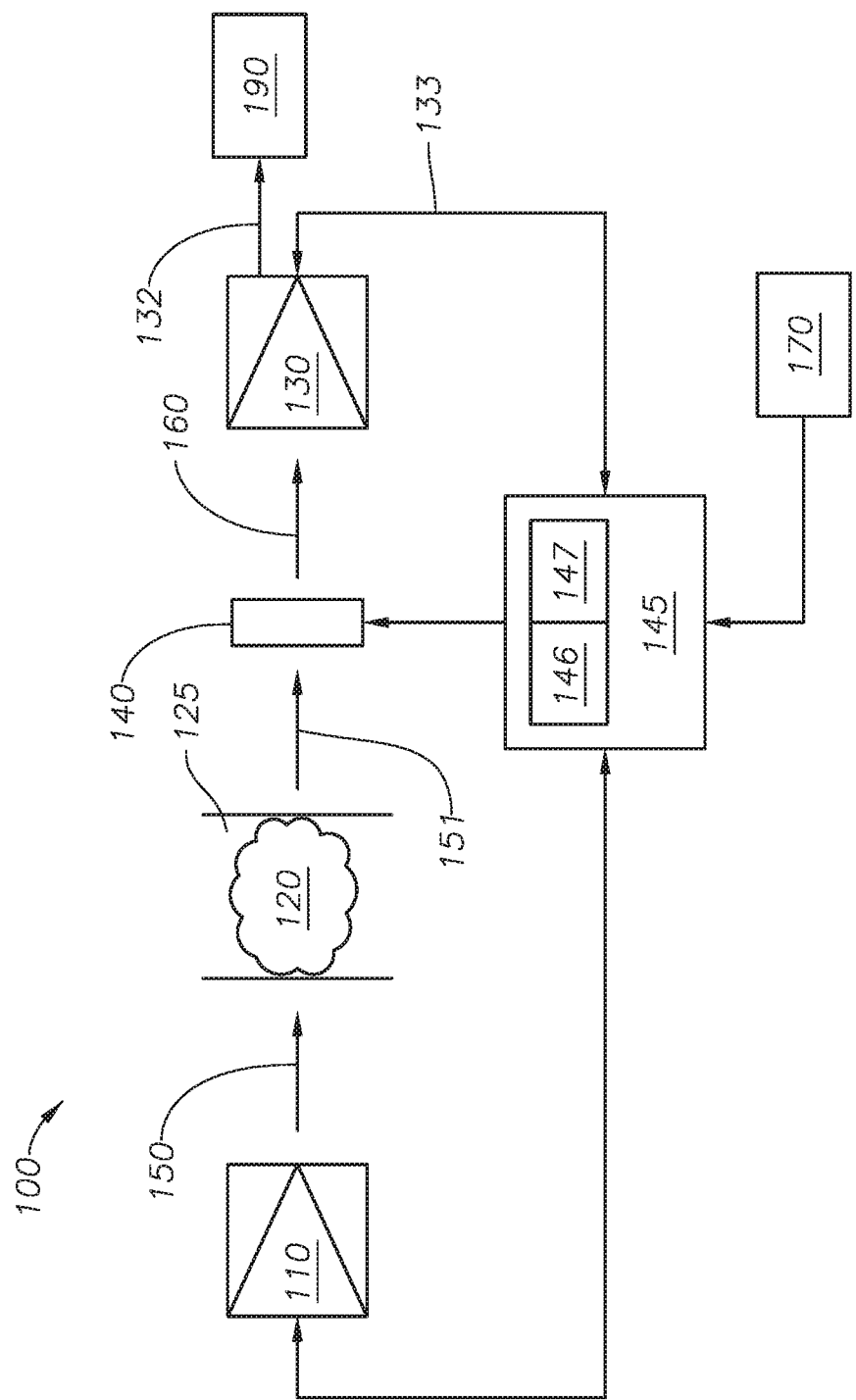
FIG. 1 shows a system to perform optical measurements on a sample, according to some embodiments.

FIG. 1 shows a system 100 to perform optical measurements on a sample 120, according to some embodiments. System 100 includes a light source 110 providing an illumination light 150 to sample 120. The particular arrangement of light source 110 depends on the sample 120 being analyzed. If the sample is transparent, illumination light 150 may be arranged to pass through sample 120. Alternatively, if the sample is opaque, illumination light 150 may be arranged to reflect or back-scatter from sample 120. Generally, sample 120 is contained in a sample containment area 125. Sample containment area 125 may be a cavity, an open or closed container, or simply a window adjacent sample 120, such as for example, a window within a conduit or tubular member in which sample 120 is contained. In some embodiments, sample 120 may be a fluid flowing in a direction, with certain speed. In some embodiments, sample 120 may be a static fluid. Further according to some embodiments sample 120 may include a powder, a mud, a colloidal suspension, an oil, a gas, a hydrocarbon, or any combination of the above. Sample 120 may further include a plurality of analytes of interest for an optical measurement.

Sample light 151 resulting from the interaction between illumination light 150 and sample 120 further interacts with a variable integrated computational element (ICE) 140. A readout sample light 160 resulting from the interaction between sample light 151 and variable ICE 140 is collected in detector 130. Detector 130 generates an output signal 132 based on readout sample light 160 which signal 132 correlates to a property of sample 120. Output signal 132 may be transmitted to an analysis unit 190 that analyzes output signal 132 in order to make a determination about one or more properties of sample 120. A controller 145 provides an electronic signal to modify the spectral properties of readout sample light 160 by adjusting the physical properties of variable ICE 140. In some embodiments, readout sample light 160 may include a portion of light transmitted through the multilayered structure in variable ICE 140. In some embodiments readout sample light 160 may include a portion of light reflected through the multilayered structure in variable ICE 140. Moreover, in some embodiments readout sample light 160 may include a portion of light transmitted or reflected from variable ICE 140.

In certain embodiments, controller 145 may be electronically coupled to one or both of light source 110 and detector 130. Thus, controller 145 may provide signals and retrieve data from light source 110 and/or from detector 130. In that regard, controller 145 may include a processor circuit 146 and a memory circuit 147. Processor circuit 146 may process data received from detector 130 and provide signals to light source 110 upon executing commands stored in memory circuit 147. Processor circuit 146 may also provide an electronic adjustment signal to variable ICE 140 in order to adjust readout sample light 160 according to a signal received from detector 130. Data received and computed by controller 145 may be temporally or permanently stored in memory circuit 147.

In some embodiments, controller 145 provides an adjustment signal to variable ICE 140 upon a signal provided by detector 130 during a calibration measurement. The adjustment signal may be used to correct variable ICE 140 during calibration. For example, signal 133 may be used to calibrate ICE 140. In some embodiments, controller 145 provides an adjustment signal to variable ICE 140 upon a signal provided by a sensor 170. Sensor 170 may be an environmental sensor, such as a temperature sensor, a pressure sensor, a humidity sensor, or a combination of the above. In some embodiments the adjustment signal provided to variable ICE 140 may adjust the spectral properties of readout sample light 160 according to physical properties of sample 120 measured by sensor 170. For example, a spectral region of interest in readout sample light 160 may depend on the density of sample 120. In this regard, an adjustment signal may be provided to variable ICE 140 in order to alter ICE 140 to measure a different property of sample of interest. Thus, ICE 140 may be configurable to function as a plurality of ICEs used in optical measurements.

Accordingly, the adjustment signal provided by controller 145 may be a voltage applied across a thickness in a multilayered film forming variable ICE 140. In some embodiments the adjustment signal may include a current made to flow through portions of variable ICE 140. In that regard, materials forming a multilayered film in variable ICE 140 may be physically sensitive to an electrical field or a magnetic field applied through the material. For example, in some embodiments variable ICE 140 includes a layer of a material that changes thickness as an electric field is applied in a direction perpendicular to the layer surface. In some embodiments, the layer of material may change thickness as a magnetic field is applied in a direction parallel to the layer surface. In embodiments where ICE 140 is configurable to function as a plurality of ICEs, voltages or currents correlating to a particular ICE configuration may be stored in memory circuit 147 so that ICE 140 may be quickly reconfigured to measure a particular property of sample 120.

Examples of materials that may be included in layers of variable ICE 140 include electrostrictive materials, piezoelectric materials, magnetorestrictive materials, and piezomagnetic materials. Electrostrictive materials include dielectric materials that suffer strain in the presence of an electric field. Some dielectrics exhibit high electrostrictive constants including; lead magnesium niobate (PMN) and lead magnesium niobate-lead titanate (PMN-PT) In some embodiments, select materials may have up to 0.1% thickness strain under the electric field produced by a 2 Volt differential. Piezoeletric materials, like lead zirconate titanate (PZT), have a select anisotropy, affected by electric field magnitude and direction. For example, a piezo-electric material layer may contract in the presence of an electric field normal to the layer surface, and expand when the electric field reverses direction. Magnetostrictive materials such as Terfenol-d may exhibit up to a 0.2% strain in the presence of a magnetic field of 2 kOe. Magnetostrictive materials may be bi-directionally sensitive to magnetic field magnitude and orientation. Piezomagnetic materials, like α $Fe2O3$, may be mechanically stressed in the presence of a magnetic field from mechanical stress or vice versa.

In some embodiments, optical measurement system 100 may be used to obtain values of a measurable property of sample 120 such as the concentration of an analyte of interest. An analyte of interest may be a hydrocarbon. In some embodiments, the measurable property may be an octane rating in a gasoline sample, or a GOR in a crude oil sample. Crude oil is a liquid containing a mixture of hydrocarbons forming oil, and dissolved gases such as methane $CH_4$, carbon dioxide, $CO_2$, and others. Hydrocarbons of interest in embodiments consistent with the present disclosure may be any one of the group including a $C_1$ hydrocarbon molecule (e.g., methane), a $C_2$ hydrocarbon molecule (e.g., ethanol), a $C_3$ hydrocarbon molecule (e.g., propane), a $C_4$ hydrocarbon molecule, a $C_5$ hydrocarbon molecule, and a $C_6$ hydrocarbon molecule (e.g., a hexane). The dissolved gases will form a gaseous phase at atmospheric conditions. Thus, when crude oil is released into the atmosphere it contains two main phases, a liquid phase which is the commonly known 'oil,' and a gas phase containing natural gas, including methane and other gases. Accordingly, the GOR of a downhole crude oil sample may indicate the value and potential use of a prospective reservoir.

Figure 2:
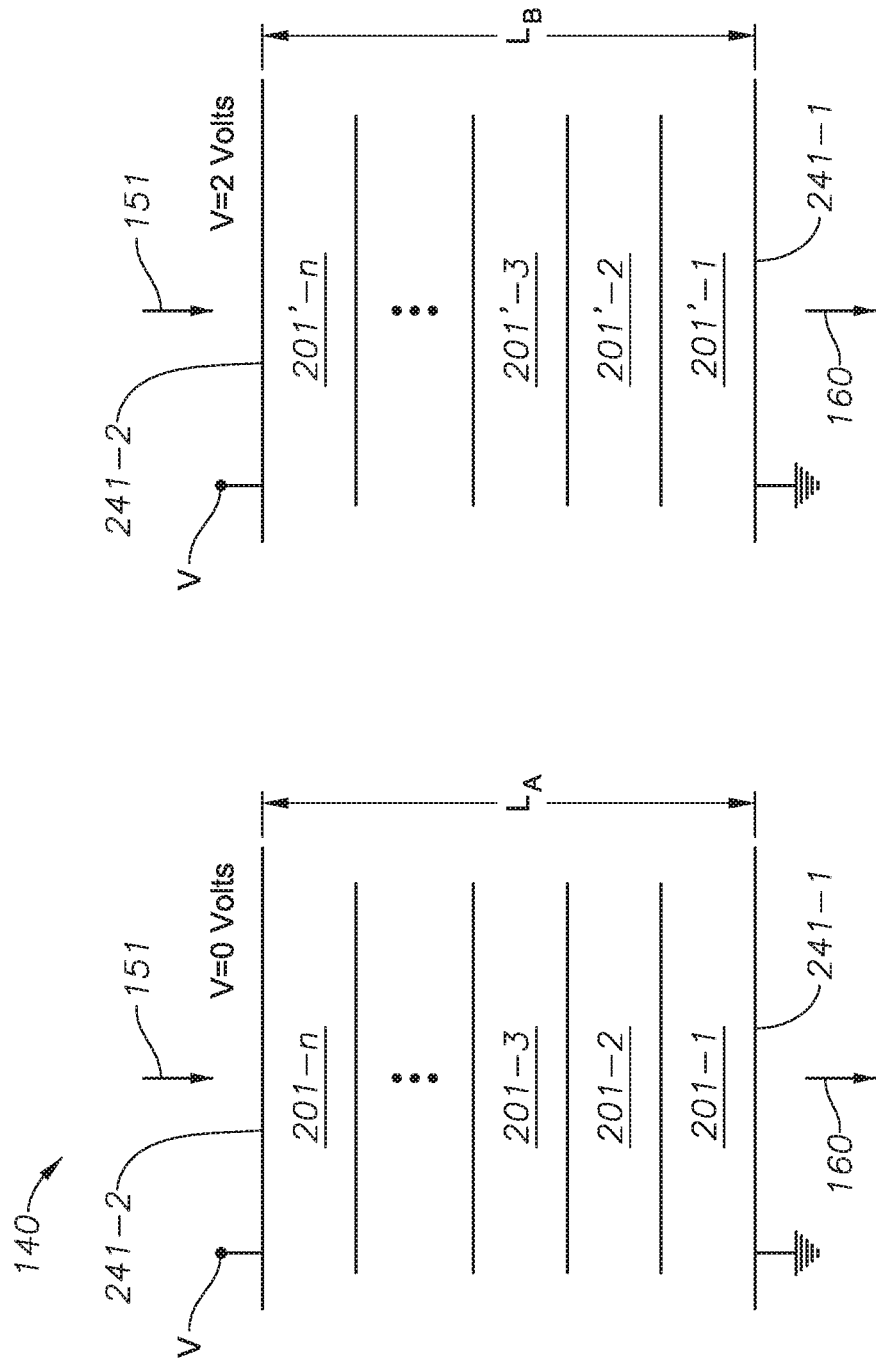
FIG. 2A shows a variable integrated computational element (ICE) according to some embodiments.
FIG. 2B shows a variable ICE according to some embodiments.

FIG. 2A shows variable integrated computational element (ICE) 140 according to some embodiments. In some embodiments, variable ICE 140 is a stack of a plurality of material layers 201-1 through 201-n, hereinafter collectively referred to as layers 201. In FIG. 2A 'n' is any positive integer. One of ordinary skill will recognize that there is no limitation to the specific value of 'n.' In some embodiments 'n' may be 10, 20, 50, 100, or even more. Each layer 201 has a preselected thickness. When ICE 140 is subject to temperature variations, thermal expansion in material causes changes in the thickness of each layer 201, resulting in changes in the refractive index of the element, hence changes in the spectral content of the optical output.

FIGS. 2A and 2B show a first electrode surface 241-1 and a second electrode surface 241-2 (hereinafter collectively referred to as electrode surfaces 241) in electrical contact with a bottom and a top surface of ICE 140, respectively. One of ordinary skill will recognize that there is nothing limiting regarding the orientation of electrode surfaces 241-1 and 241-2 as 'bottom' or 'top'. In general, the orientation of multilayered variable ICE 140 may be vertical, horizontal, or any other suitable orientation. Electrode surfaces 241 are on opposite sides of a thickness of multilayered variable ICE 140. In some embodiments, electrode surfaces 241 are made of an electrically conductive material that is transparent to light. Such materials may be indium tin oxide (ITO) or others (i.e. fluorine doped tin oxide (FTO) or carbon nanotubes) well known in the art. Accordingly, it may be desirable that at least one of electrode surfaces 241 be transparent to light in the UV, VIS, NIR, MIR spectral regions, or any combination of the above. Generally light passes through ICE 140 such that the light is substantially perpendicular to the surface of multilayered variable ICE 140. As illustrative, sample light 151 is shown passing through ICE 140 to produce readout sample light 160.

By applying a voltage difference between electrodes 241-1 and 241-2, an electric field substantially perpendicular to the surface of multilayered variable ICE 140 may be formed. In FIGS. 2A and 2B the bottom electrode surface 241-1 is electrically coupled to ground, while a voltage V is electrically coupled to top electrode surface 241-2. In some embodiments top surface 241-2 may be electrically coupled to ground, and bottom surface 241-1 may be coupled to a voltage V, without loss of generality. Voltage V may be positive or negative. Under a zero voltage, the thickness of multilayered variable ICE 140 is $L_A$.

FIG. 2B shows variable ICE 140 with a voltage, V=2 Volts, applied to top electrode surface 241-2. An electric field in a direction substantially perpendicular to the surface of multilayer 140 is thus formed. As a result, some or all of layers 201 suffer a contracting strain, reducing their thickness and forming layers 201'. Accordingly, a contraction of the multilayer thickness from $L_A$ to $L_B$ is produced by the presence of the electric field across the multiple layers 201. A smaller thickness $L_B$ may result from the contraction of each or some of layers 201. In that regard, the contraction of thickness $L_A$ to $L_B$ modifies the spectral properties of a light passing through variable ICE 140 in the direction of the electric field (e.g., sample light 151, cf. FIG. 1). For example, one of layers 201-$i$ (T being any integer between 1 and 'n') may include a ¼ wave filter having a thickness of 4.000 μm (1 μm=$10^{-6}$ m) centered at a wavelength $\lambda_i$ under zero voltage conditions (thickness $L_A$, FIG. 2A). Once the voltage is applied forming the electric field, layer 201-$i$ may contract by 2 nm into layer 201'-$i$ having a thickness of 3.998 μm. This corresponds to a strain of 0.05% of the material in layer 201-$i$. Under such conditions, the center wavelength X blue shifts by about 8 nm, so that the new center wavelength of layer 201'-I is $\lambda_i'=\lambda_i-8$ (in nm). One of ordinary skill in the art will recognize that the above dimensions are exemplary only, and other thickness changes may be produced in embodiments as disclosed herein. Further, in some embodiments the thickness of multilayered ICE 140 may be increased (i.e., $L_A<L_B$) upon the application of an electric field, or a magnetic field.

In some embodiments, an electrostrictive compensation approach may include multilayered variable ICE 140 having predominantly dielectric materials in layers 201. Applying an electric field to "squeeze" the layer stack to reduce multilayer thickness may compensate thermally induced expansion during operation of an optical measurement system (e.g., system 100, cf. FIG. 1). In some embodiments, a servo mechanism in controller 145 may be implemented so that the electrostatic field applied to multilayered variable ICE 140 compensates for temperature variations. For example, sensor 170 may be a temperature sensor providing a temperature reading to controller 145. Controller 145 may store a temperature correlation chart in memory 147. Thus, for any given temperature a voltage applied to variable ICE 140 results in a thickness adjustment compensating thermal strain. Thus, in some embodiments variable ICE 140 may be a "Temperature Flat" i.e., response of the optical element with much reduced temperature sensitivity.

In some embodiments electrostrictive squeezing of variable ICE 140 substantially "blue shifts" the spectral properties of readout sample light 160. The shift will be a function of the layer thickness and a response function to the field as exemplified above with a ¼ wave filter in layer 201-$i$. The response function is an inherent property of the material (e.g., an electrostrictive constant, or a magnetostrictive constant). In some embodiments, different electric fields may be provided to different portions of variable ICE 140, thus refining the adjustment of spectral properties of readout sample light 160.

The spectroscopic response function for each layer 201 is thus controllable. In some embodiments, layers 201 may include piezoeletric materials such that the polarity and magnitude of the voltage may expand or contract the layer thickness depending on the polarity of the applied voltage. Thus, the spectral properties of readout sample light 160 may be blue shifted or red shifted, as desired. Magnetostrictive, piezoelectric, or piezomagnetic materials can be used in place of, or in combination with, electrostrictive materials in much the same way. One can also combine electrostrictive, magnetostrictive piezoelectric, or piezomagnetic materials in some embodiments of variable ICE 140.

Figure 3:
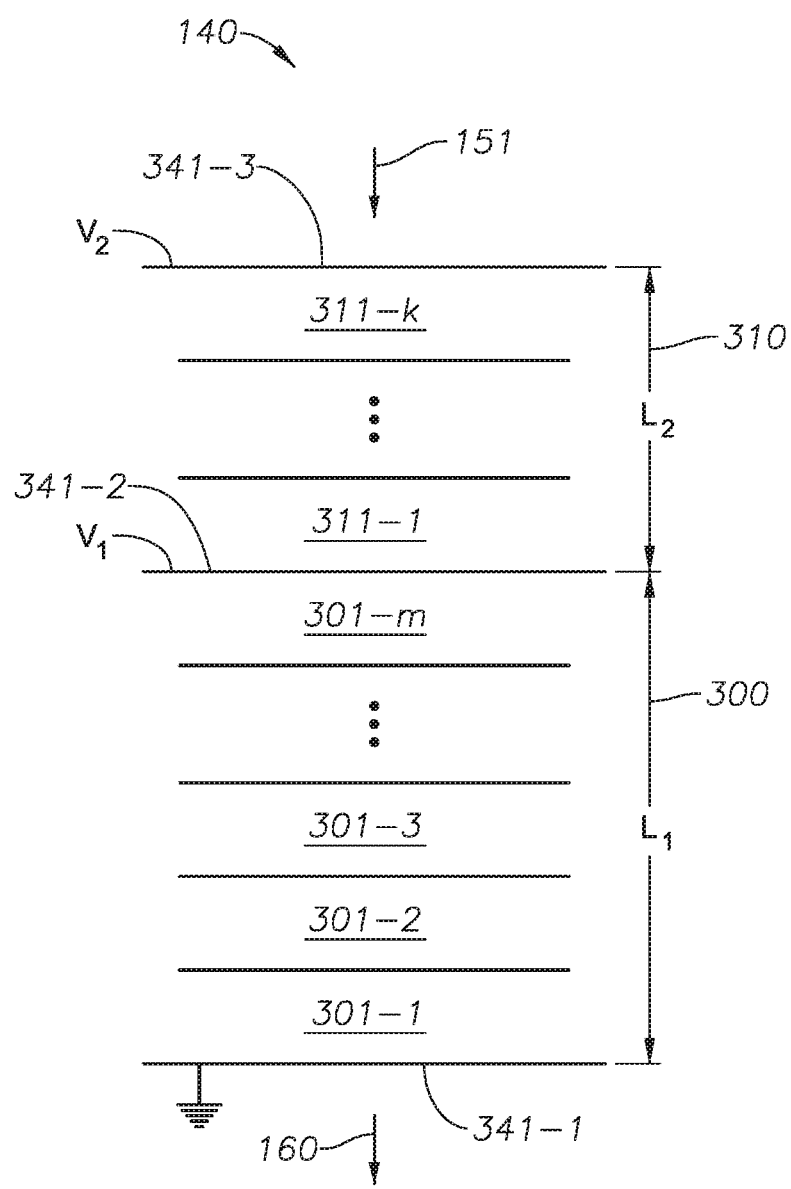
FIG. 3 shows a variable ICE according to some embodiments.

FIG. 3 shows variable ICE 140 according to some embodiments. Variable ICE 140 may include a first portion 300 including layers 301-1 through 301-$m$ (collectively referred hereinafter as layers 301), having a thickness $L_1$. Variable ICE 140 may also include a second portion 310 including layers 311-1 through 311-$k$ (collectively referred hereinafter as layers 311), having a thickness $L_2$. The values 'm' and 'k' may be any positive integer, without loss of generality. Variable ICE 140 may include electrode surfaces 341-1, 341-2, and 341-3 (collectively referred hereinafter as electrode surfaces 341). Electrode surfaces 341-1 and 341-2 provide a first electric field to first portion 300, and electrode surfaces 341-2 and 341-3 provide a second electric field to second portion 310. Electrode surfaces 341 may be as electrode surfaces 241, described in detail above (cf. FIGS. 2A and 2B). The response of each layer 301 and each layer 311 can be separately controlled by applying different voltages across portion 300 and across portion 310.

Thus, variable ICE 140 may be controlled such that upon application of a first electric field, thickness $L_1$ changes by a first strain proportion. Likewise, upon application of a second electric field, thickness $L_2$ changes by a second strain proportion. In general, the first strain proportion and the second strain proportion may be different. In some embodiments, either one of the first strain proportion and the second strain proportion may be zero. Furthermore, in some embodiments the first strain proportion may be opposite in sign to the second strain proportion. That is, in some embodiments the first electric field and the second electric field may be such that the first portion of variable ICE 140 expands while the second portion of variable ICE 140 contracts, or vice versa. Thus, by changing the strain proportion in different portions of variable ICE 140 a first portion of the spectrum of readout sample light 160 may be blue shifted while a second portion of the spectrum of readout sample light 160 may be red shifted. For example, when a fabrication variance in variable ICE 140 is detected during a calibration procedure, the variance may be corrected by applying a blue shift in a first portion of the spectrum and applying a red shift in a second portion of the spectrum. Persons of skill in the art will appreciate that multiple electrodes and multiple electrically responsive layers 301 may be interleaved or alternated as desired to achieve the a desired optical result. In this regarded, each layer 301 may be bounded by an electrode in order to control layers individually.

A temperature change may induce changes in the refractive index of the dielectric materials included in a multilayered structure forming variable ICE 140. Also, temperature changes induce contracting and expanding strains in the multilayered structure forming variable ICE 140 as a function of the material's expansion coefficients. A change in spectral properties of readout sample light 161 induced by temperature variations may include refractive index changes and strain. Accordingly, in some embodiments, spectral shifts induced by refractive index changes are marginal in comparison to spectral shifts induced by strain. This will be described in more detail below, in relation to FIG. 4.

Figure 4:
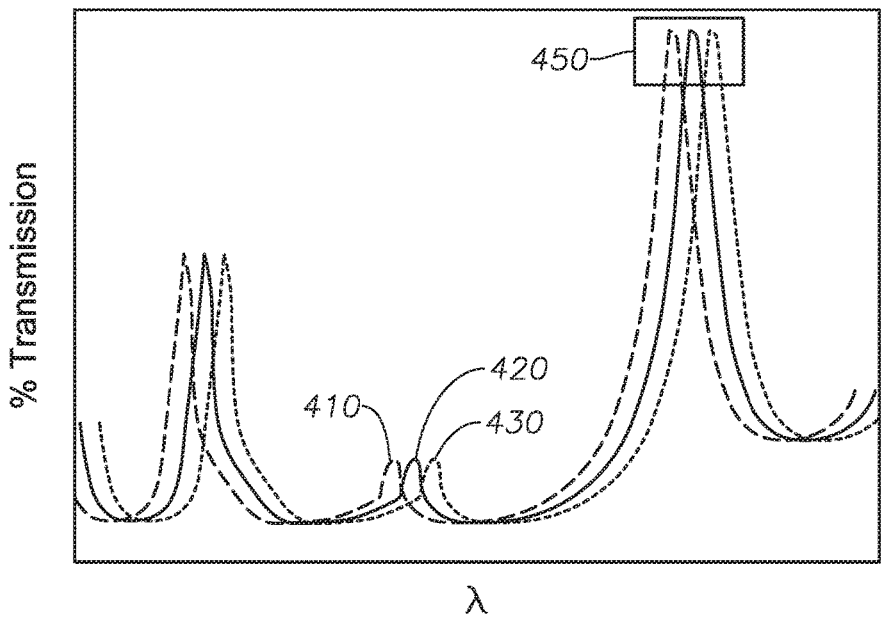
FIG. 4 shows transmission spectra of a sample light through a variable ICE according to some embodiments.

FIG. 4 shows transmission spectra 410, 420, and 430 of a sample light 151 through variable ICE 140, according to some embodiments. The ordinate axis in FIG. 4 corresponds to a percent transmission of light passing through variable ICE 140. The abscissa axis in FIG. 4 corresponds to a wavelength λ of the transmitted light. The spectral region covered by the abscissa in FIG. 4 may be the UV, VIS, NIR, MIR spectral region or any combination of the above. Spectra 410, 420, and 430 correspond to different strain conditions in variable ICE 140. Spectrum 410 is blue shifted with respect to spectrum 420, and corresponds to a proportional strain of about −0.2% (contraction) relative to a zero strain condition (spectrum 420). Spectrum 430 is red shifted with respect to spectrum 420, and corresponds to a proportional strain of about 0.2% (expansion) relative to zero strain. Strain in variable ICE 140 may be the result of an environmental variation such as a temperature change, or an induced electrical or magnetic field from a signal provided by controller 145. A variable ICE 140 as in FIG. 4 has a number 'n' of layers equal to 13. One of ordinary skill recognizes that n=13 is only an exemplary embodiment used in FIG. 4 for illustration purposes. Variable ICE 140 may have any number 'n' of layers without loss of generality. FIG. 4 also shows a detail 450 of transmission spectra 410, 420, and 430, which will be discussed in more detail in relation to FIG. 5, below.

Figure 5:
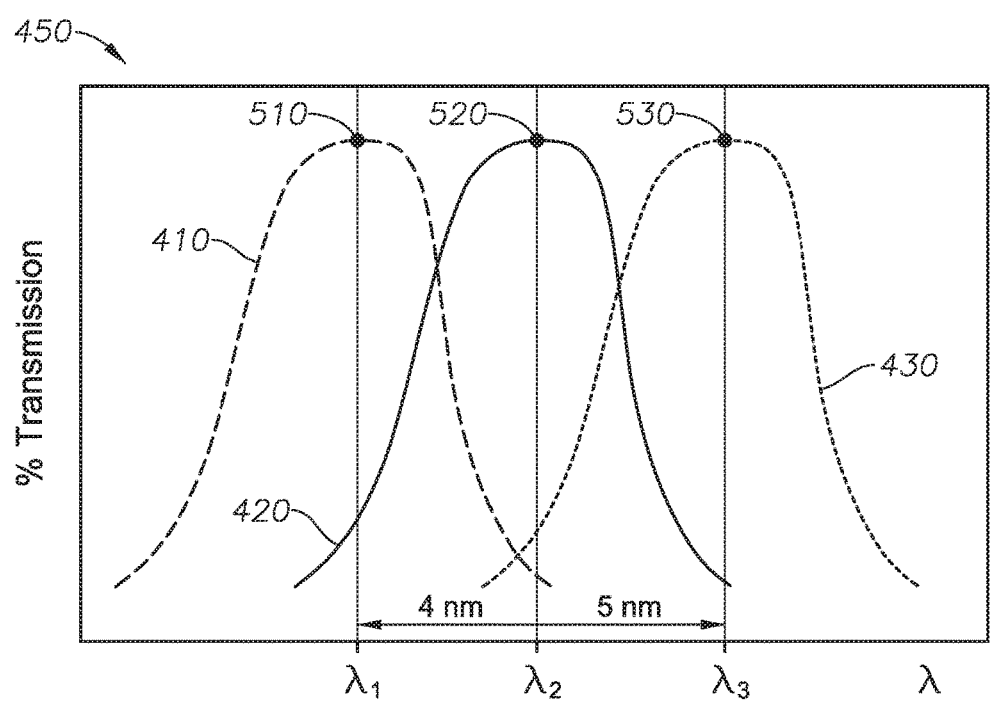
FIG. 5 shows a detail of transmission spectra of a sample light through a variable ICE according to some embodiments.

FIG. 5 shows detail 450 of transmission spectra 410, 420, and 430 of sample light 151 through variable ICE 140, according to some embodiments. The abscissa in FIG. 5 shows an expanded long wavelength X region from about 2258 nm to about 2290 nm (in the NIR region). Accordingly, FIG. 5 shows transmission peaks 510, 520, and 530 of spectra 410, 420, and 430, in detail 450, respectively. FIG. 5 illustrates that by contracting layer thickness, the spectrum of variable ICE 140 is blue-shifted, shifting center wavelength λ of peak 510 to the left of center wavelength $\lambda_2$ of peak 520, by about 4 nm. FIG. 5 also shows that by increasing the layer thickness, the spectrum of variable ICE 140 is red-shifted, moving center wavelength $\lambda_3$ of peak 530 to the right of center wavelength $\lambda_2$ of peak 520, by about 5 nm. Thus, a range of about 9 nm in shift can be obtained for variable ICE 140 including 13 dielectric layers over a 0.4% proportional strain (±0.2% thickness from the original).

In some embodiments, optical measurement system 100 may perform a calibration measurement to adjust variable ICE 140. In a calibration measurement, the response of system 100 is obtained for a set of know standard samples 120. For example, the set of known standard samples may have a gradation of an analyte concentration, which may be a measurable quantity for which variable ICE 140 is configured. The gradation of concentration values in the calibration samples may form a vector (y). Using optical measurement system 100 a set of signals (x) may be obtained from the calibration samples. Variable ICE 140 is designed such that analyte concentrations (y') may be obtained using $$y' = G \cdot x + 0 \tag{1}$$

Where G is a pre-selected slope and O is a pre-selected offset value particular to a design of variable ICE 140. A qualifying measure of the performance of variable ICE 140 is obtained by comparing y' with y, in the calibration samples. For example, a qualifying measure may be a standard error of calibration (SEC), which is the square root of the sum of squared differences between y and y' for a number of calibration samples (p).

$$SEC = \sqrt{\frac{\Sigma(y - y')^2}{p}} \tag{2}$$

Table 1 below details thickness data (in nm, 1 nm=$10^{-9}$ m) for the 13 layers in variable ICE 140 used in the spectral results depicted in FIGS. 4 and 5. Variable ICE 140 as used in the exemplary embodiment for FIGS. 4 and 5 includes alternating layers of material having high (201-$i$ layers with T odd) and low refractive index (201-$j$ layers with T even). Accordingly, Table 1 includes a column for variable ICE 140 strained by −0.2% (left), no strain (center), and strained by +0.2% (right). According to some embodiments, a proportional strain by ±0.2% is about the expected environmentally induced strain in field applications including oil exploration and extraction. A proportional strain of about ±0.2% may be obtained in embodiments as disclosed herein using electrostrictive, magnetostrictive, piezoelectric, or piezomagnetic materials.

Table 1 shows that the SEC for the original design (no strain) is 0.446 units, using the original G and O values (cf. Eqs. (1) and (2)). As variable ICE 140 is modeled to expand (+0.2% strain) and contract (−0.2% strain), SEC values are calculated using Eqs. (1) and (2). Table 1 illustrates how the measurement performance of system 100 degrades under environmental stress when no re-calibration adjustments are performed. As shown in Table 1, the SEC increases to 2.09 and 2.25 units for the contracted (−0.2% strain) and expanded (+0.2%) cases, respectively.

Using electrostrictive, magnetostrictive piezoelectric, or piezomagnetic materials in variable ICE 140 as disclosed herein, performance degradation of optical measurement system 100 due to environmental strain may be compensated in real time. Accordingly, some embodiments of system 100 may implement a feedback loop in controller 145, whereby after a certain number of measurements or upon crossing a threshold measurement in sensor 130, a calibration step is carried out. In the calibration step a number of standard samples with known concentrations y are processed to obtain measured concentrations y'. A SEC value is calculated using Eqs. (1) and (2). When the SEC value departs from a minimum design value, controller 145 sends a correcting signal to variable ICE 140. The correcting signal may be a voltage to produce a contraction (negative strain) or an expansion (positive strain) on the multilayered stack in variable ICE 140. In some embodiments, the correcting signal may be a plurality of voltages provided to a plurality of portions in variable ICE 140. Further according to some embodiments, the correcting signal may be a current providing a magnetic field within the multilayered stack in variable ICE 140. A subsequent processing of calibration samples is performed, new measured concentrations y' are obtained, and the SEC value calculated to ensure that the minimum design value is recovered.

TABLE 1

| layer | −0.2% | Original | +0.2% |
|---|---|---|---|
| 1 | 286.84 | 287.42 | 287.99 |
| 2 | 618.64 | 619.88 | 621.12 |
| 3 | 512.75 | 513.77 | 514.80 |
| 4 | 20.54 | 20.58 | 20.62 |
| 5 | 58.41 | 58.53 | 58.64 |
| 6 | 257.33 | 257.84 | 258.36 |
| 7 | 243.49 | 243.98 | 244.46 |
| 8 | 483.25 | 484.22 | 485.19 |
| 9 | 643.99 | 645.28 | 646.57 |
| 10 | 272.08 | 272.62 | 273.17 |
| 11 | 386.63 | 387.40 | 388.18 |
| 12 | 141.11 | 141.39 | 141.67 |
| 13 | 175.48 | 175.83 | 176.18 |
| SEC | 0.439 | 0.446 | 0.455 |
| ΔA/B | 1.604 | 1.568 | 1.524 |
| SEC (orginal G and O) | 2.089 | 0.446 | 2.246 |

Likewise, rather than correcting ICE 140 based on a feedback loop, ICE 140 may be adjusted, using electrostrictive, magnetostrictive piezoelectric, or piezomagnetic materials forming the layers of ICE 140, in order to alter ICE 140 in real time to measure a different property of a sample being analyzed. This is particularly useful in environments, such as downhole, where it is not feasible to physically substitute one ICE for another in order to measure a different property.

Figure 6:
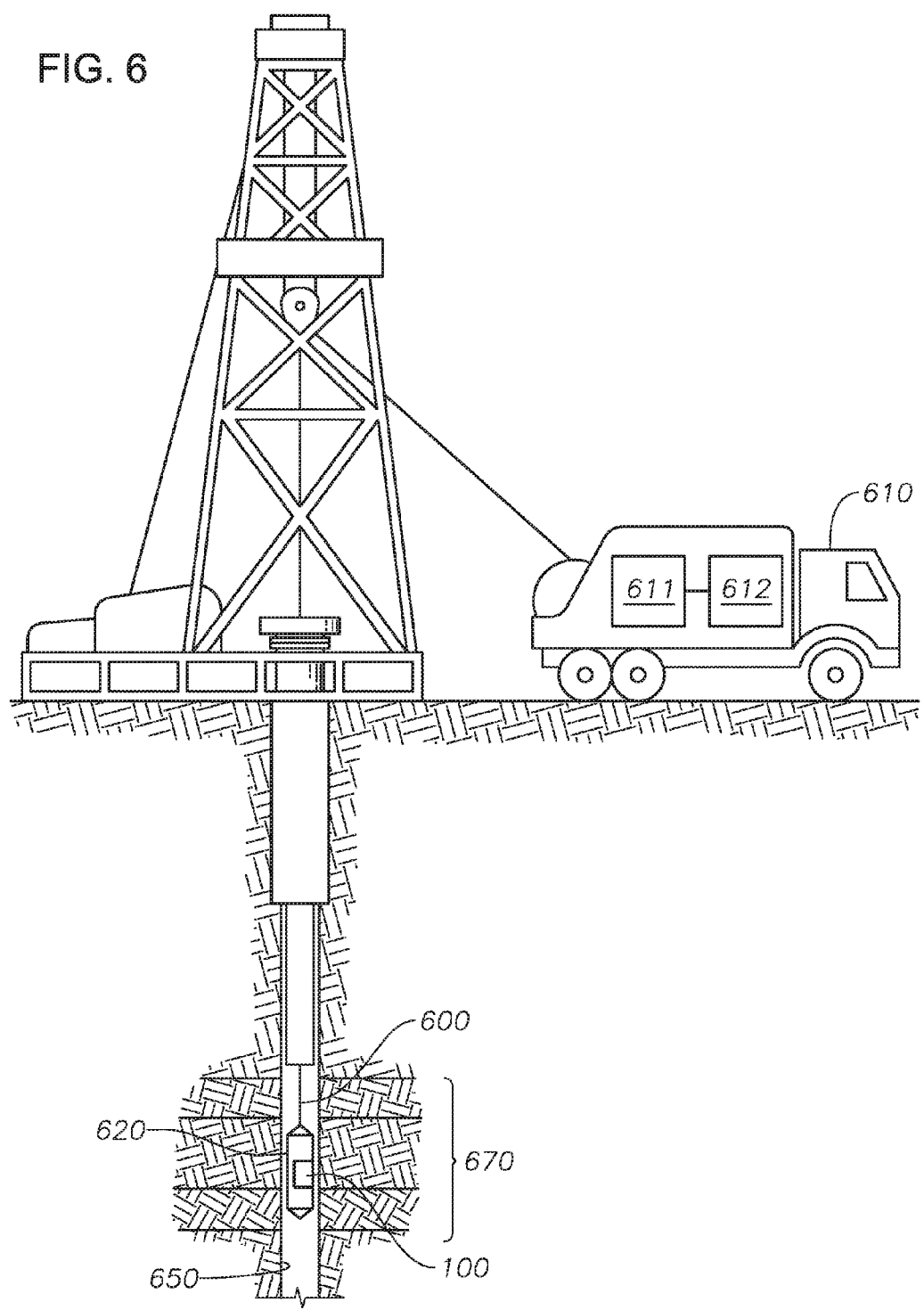
FIG. 6 shows a system to perform an optical measurement of a sample in a wireline logging application, according to some embodiments.

FIG. 6 shows a system to perform an optical measurement of a sample in a wireline logging application, according to some embodiments. Wireline logging includes measurements of fluids and substrates in wellbores drilled for oil and hydrocarbon exploration. In some embodiments, a surface unit 610 includes a processor circuit 611 and a memory circuit 612 to provide commands for sensor package 620 to perform measurements and store data obtained from the measurements. In certain embodiments, surface unit 610 may be a movable surface unit, such as a vehicle. Once a wellbore 650 has been drilled, wireline measurements may be performed by introducing sensor package 620 into wellbore 650, using a wireline 600. Wellbore 650 may traverse through a ground formation 670. Sensor package 620 may have one or more components of an optical measurement system 100, which may include a light source, a variable ICE 140 and a detector 130, as disclosed in various embodiments herein. Furthermore, sensor package 620 may include a portion of an optical delivery system to deliver input light 150 and a portion of an optical collection system to collect sample light 151 (cf. FIG. 1). In some embodiments, a portion of the light delivery system, such as light source 110, may be included in surface unit 610. Likewise, a portion of the optical collection system, such as detector 130, may be included in surface unit 610, such as detector 130 and analysis unit 190. In some embodiments, the optical delivery system and the optical collection system may include an optical fiber, or fiber bundle. The optical fiber or fiber bundle carries input light 150 and sample light 151 along wireline 600.

Figure 7:
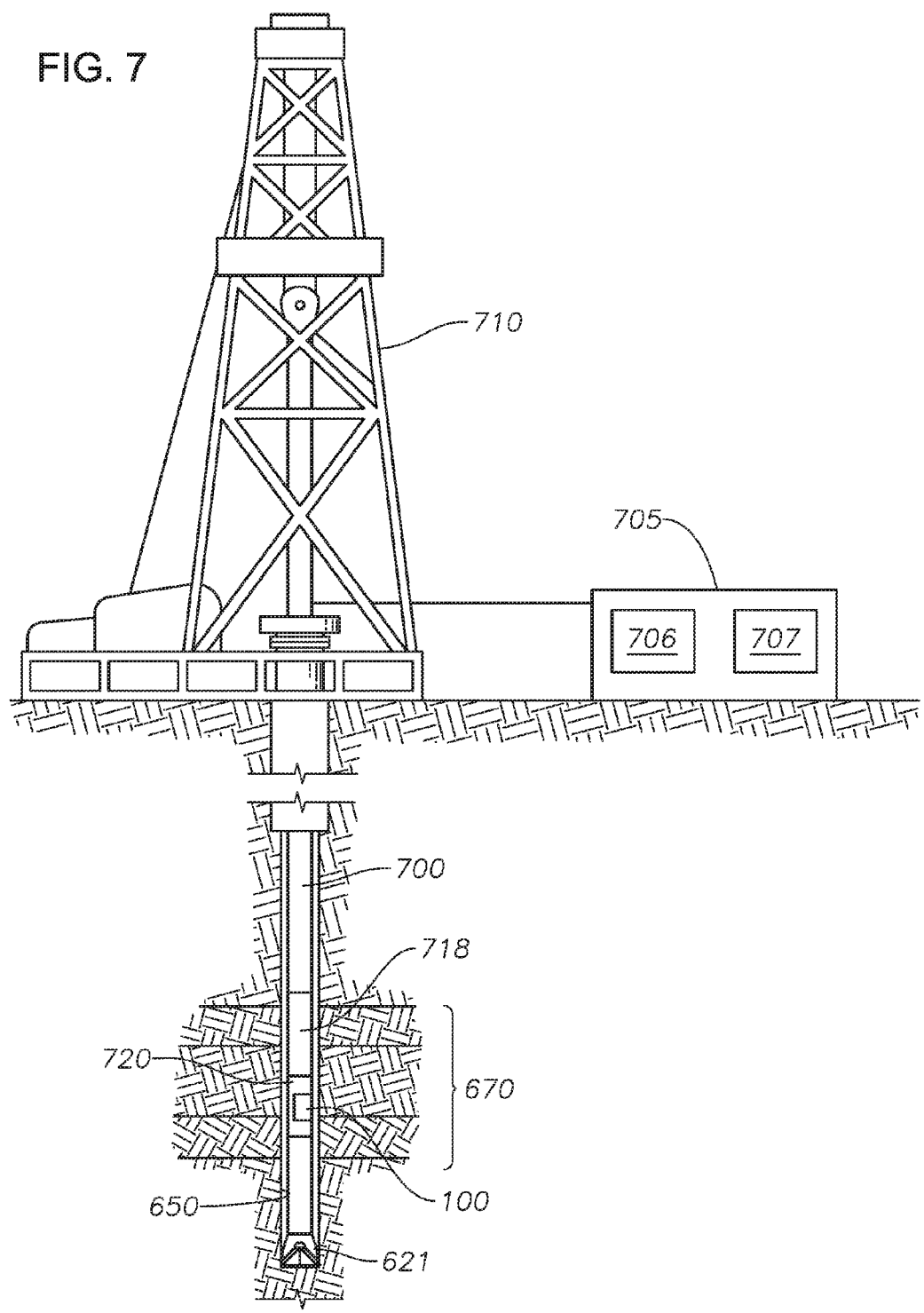
FIG. 7 shows a drill bore including a sensor in a system to perform an optical measurement in a sample for a logging-while-drilling (LWD) application, according to some embodiments.

FIG. 7 illustrates the deployment of an optical measurement system 100 during wellbore drilling operations, permitting logging-while-drilling (LWD) application of system 100, according to some embodiments. An LWD configuration performs desired measurements, such as acoustic, electromagnetic and optical data, while a wellbore is being drilled. According to FIG. 7, a drill string 700 carries a bottom hole assembly 718 which includes a drill bit—621 utilized to drill a wellbore 650—, traversing through ground formation 670. Drilling operations—may be operated by a controller 705 which may be positioned at the surface, as shown, or locally in bottom hole assembly 718. A drilling rig 710 provides structural support to drill string 700. Controller 705 may include a processor circuit 706 and a memory circuit 707. Memory circuit 707 stores commands and data used by processor circuit 706 to control drilling operations, such as controlling one or more functions of bottom hole assembly 718. Bottom hole assembly 718 includes a sensor package 720. Sensor package 720 includes one or more components of an optical measurement system 100, as described in various embodiments herein, for measuring characteristics of fluids in wellbore 650, which fluids may include drilling fluids, such as drilling mud, as well as formation fluids, such as hydrocarbons.

Figure 8:
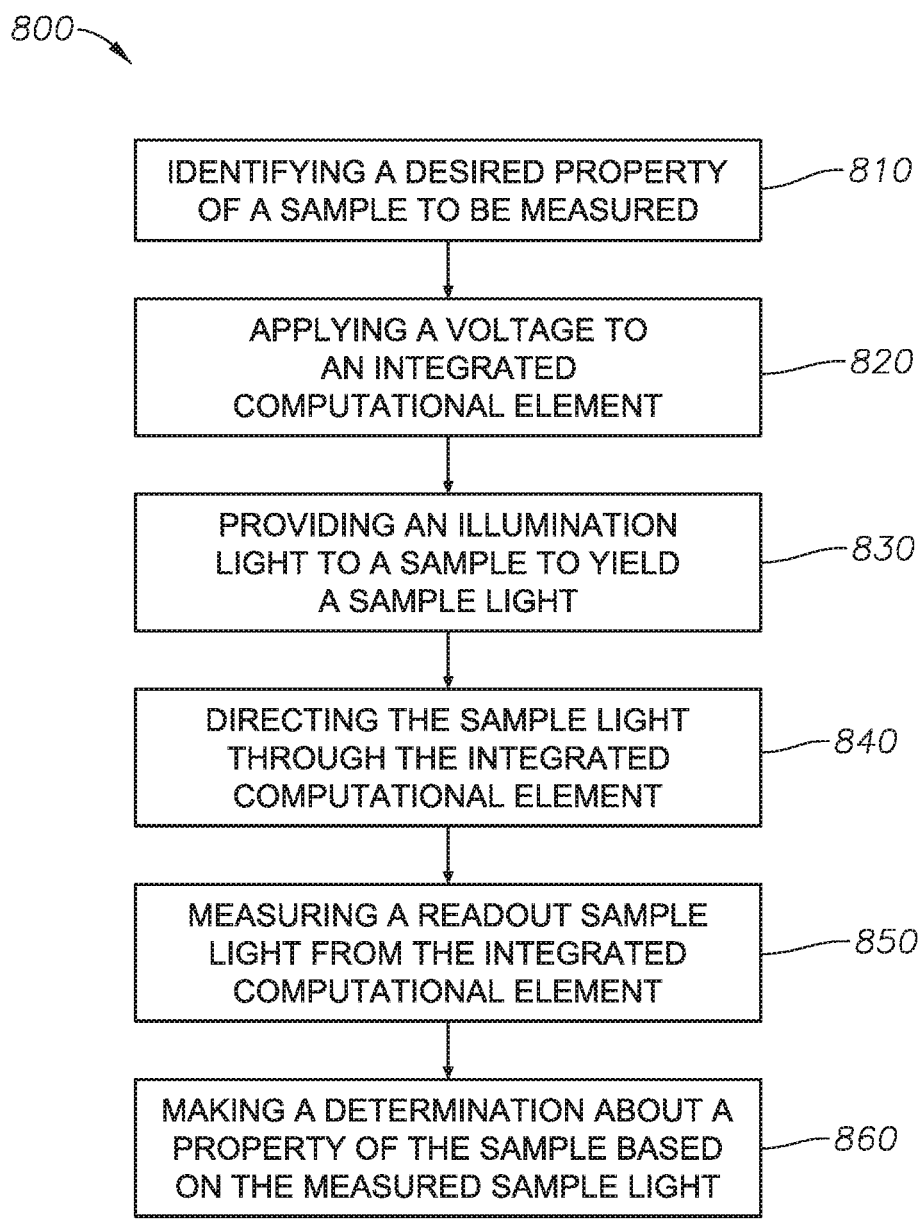
FIGS. 8 and 9 show flow charts of a method for measuring properties of a sample using a variable ICE, according to some embodiments.
Figure 9:
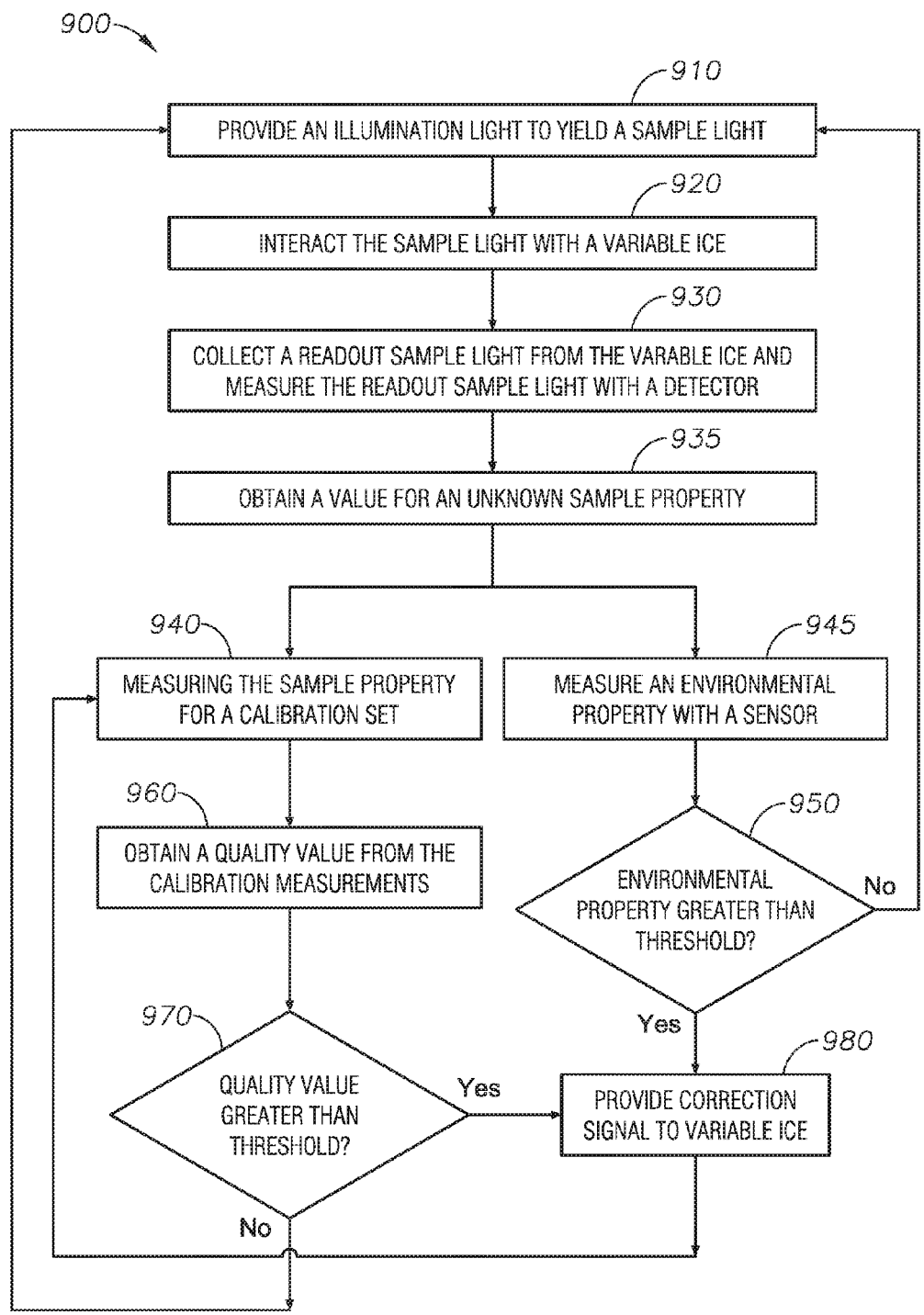

FIGS. 8 and 9 shows a flow charts of a method 800, 900 for measuring properties of a sample using variable ICE (e.g., variable ICE 140, cf. FIG. 1), according to some embodiments. Accordingly, steps in method 800, 900 may be partially or totally performed by a controller in an optical measurement system, the controller using a processor circuit executing commands stored in a memory circuit (e.g., optical measurement system 100, controller 145, processor circuit 146, and memory circuit 147, cf. FIG. 1). Steps in method 800, 900 may also be partially or totally performed by an operator controlling the optical measurement system using a computer including a processor circuit and a memory circuit. The optical measurement system may also include a light source, a detector, and an environmental sensor (e.g., light source 110, detector 130, and environmental sensor 170). All or a portion of the steps may be performed in a wellbore. A portion of the steps may also be performed at the earth's surface adjacent a wellbore.

With particular reference to FIG. 8, step 810 includes identifying a desired property of a sample to be measured. As mentioned above, a particular ICE is selected to correspond to a particular property of sample. Thus, it is necessary to identify the desired property for measurement. This in turn permits identification of a particular ICE configuration. In step 820, a voltage or magnetic field is applied to a variable ICE. This alters the optical properties of the variable ICE so that the variable ICE corresponds with the particular sample property under investigation. In this regard, the variable ICE may be formed of one or more layers of film that is physically sensitive to an electrical field or a magnetic field applied through the material. For example, the film may be a layer of a material that changes thickness as an electric field is applied in a direction perpendicular to the layer surface. In some embodiments, the layer of material may change thickness as a magnetic field is applied in a direction parallel to the layer surface. In this regard, the film may be formed of electrostrictive materials, piezoelectric materials, magnetorestrictive materials, and/or piezomagnetic materials. Under application of a voltage or magnetic field, the thickness of one or more layers may be altered, thereby altering the optical properties of the ICE. For example, a layer and/or the overall ICE itself may be red-shifted or blue-shifted as desired.

Step 830 includes providing an illumination light to a sample. The illumination light source may be local to the sample or the illumination light may be transmitted to the sample via an optical fiber. Step 830 may include using the light source to provide the illumination light. In some embodiments, the illumination light in step 830 may be provided by environment light, such as the sun, room light, or any other natural source. The illumination light interacts with the sample to yield a sample light. The illumination light may be transmitted through a portion of the sample or reflected from a portion of the sample, or a combination of the two.

In step 840, the sample light is directed through the ICE to which the voltage or magnetic field has been applied. The resulting readout sample light can then be measured, such as illustrated in step 850. Based on the measured sample light, in step 860, a determination about a property of the sample can be made.

Method 800 may include one or more feedback loops, such as a calibration feedback loop or an environmental feedback loop which feedback may alter the voltage or magnetic field applied to the ICE. Such feedback loops are described above and illustrated more particularly in method 900.

With reference to FIG. 9, step 910 includes providing an illumination light to a sample, thereby yielding a sample light. The source of the illumination light may be local to the sample or the illumination light may be transmitted to the sample via an optical fiber. Step 910 may include using the light source to provide the illumination light. In some embodiments, the illumination light in step 910 may be provided by environment light, such as the sun, room light, or any other natural source. Step 920 includes interacting the sample light with the variable ICE. In some embodiments, step 920 may include transmitting a portion of the sample light through the variable ICE, or reflecting a portion of the sample light from the variable ICE, or a combination of transmitting and reflecting the sample light with the variable ICE.

Step 930 includes collecting a readout sample light from the variable ICE and measuring the readout sample light with a detector. The readout sample light results from the interaction between the sample light and the variable ICE. Step 935 includes obtaining a value for an unknown sample property using a signal produced in the detector by the readout sample light. For example, step 935 may include using a detector signal 'x' to obtain a value 'y' for a measurable property of the sample, using Eq. (1) above. At this point, a determination about a property of the sample can be made where the optical characteristics of the variable ICE are within a desired threshold. To the extent the ICE requires calibration, step 940 may be performed. Likewise, to the extent the ICE is subject to undesired changes due to the environment in which the ICE is deployed, step 945 may be perfomed.

Accordingly, step 945 includes measuring an environmental property with a sensor. Step 945 may include measuring a temperature, a pressure, or other physical property of the measurement setup. For example, in some embodiments step 945 may include measuring humidity.

When the environmental property measured in step 945 is beyond a pre-selected threshold according to step 950, step 990 includes providing an adjustment signal to the variable ICE to alter the electric or magnetic field. The pre-selected threshold may be a change in temperature, a change in pressure, or a change in humidity in the environment, relative to a previous measurement. Thus, step 980 may include providing an electronic signal, such as a voltage or a current, to the variable ICE. Furthermore, in some embodiments step 980 may include providing two or more voltages to the variable ICE.

To the extent calibration is desired, step 940 includes measuring the sample property for a calibration set. Step 940 may include providing a calibration set having a plurality of standardized samples. For example, when the measurable property is an analyte concentration, the standardized samples may be a set of samples including a graduated and precisely known analyte concentration. Step 960 includes obtaining a quality value from the calibration measurements in step 940. Accordingly, step 960 may include obtaining a SEC value from the calibration measurements using Eqs. (1) and (2) above.

When the quality value obtained in step 960 is determined to be greater than a threshold in step 970, step 980 follows, as described in detail above. Accordingly, steps 940, 960, 970, and 980 may be performed in the optical measurement system with a periodicity that is lower than obtaining the value of the unknown sample property in step 935. In some embodiments, steps 940, 960, 970, and 980 may be performed upon determining in step 950 that an environmental property is greater than a threshold. For example, when a temperature or pressure measurement indicates a change in environmental conditions, a new calibration set may be desirable. When environmental conditions change, optical alignment of the system may be altered, or the variable ICE may be misaligned, or strained. In such situations, it may be desirable to re-calibrate the system and provide a adjustment signal to the variable ICE if necessary.

The sample may include liquids, solids or gases or a combination thereof and comprise hydrocarbons flowing from the formation and/or drilling fluids injected into the wellbore. In this regard, additional steps may include practicing the foregoing steps my deploying one or more components of the variable ICE system in a wellbore, either on a wireline or while drilling.

Embodiments described herein are exemplary only. One skilled in the art may recognize various alternative embodiments from those specifically disclosed. Those alternative embodiments are also intended to be within the scope of this disclosure. As such, the embodiments are limited only by the following claims.

What is claimed is:

1. A variable integrated computational element (ICE) for optical measurement of a property of a sample, the ICE comprising:
    a plurality of layers of a dielectric material;
    a transparent electrode adjacent to the layers of dielectric material;
    a second electrode adjacent to the layers of dielectric material, opposite to the transparent electrode; wherein the dielectric material is strained in the presence of an electromagnetic field.

2. The variable ICE of claim 1, further wherein the dielectric material is selected from the group consisting of an electrostrictive material, a magnetostrictive material, a piezoelectric material, and a piezomagnetic material.

3. The variable ICE of claim 1, wherein the transparent electrode and the second electrode are configured to provide an electric field through the plurality of layers.

4. The variable ICE of claim 1 wherein the transparent electrode and the second electrode are configured to receive a first voltage and a second voltage, respectively.

5. The variable ICE of claim 1, wherein the transparent electrode and the second electrode are configured to provide a magnetic field through the layers of a dielectric material.

6. The variable ICE of claim 5, wherein the transparent electrode and the second electrode are configured to receive a current.

7. The variable ICE of claim 1 further comprising:
a second plurality of layers of a dielectric material adjacent to the transparent electrode; and
a second transparent electrode adjacent to the second layers of a dielectric material, opposite to the transparent electrode.

8. The variable ICE of claim 7, further wherein the second layers of a dielectric material are selected from the group consisting of an electrostrictive material, a magnetostrictive material, a piezoelectric material, and a piezomagnetic material.

9. An optical measurement system for measuring a property of a sample, the system comprising:
a light source to provide an illumination light to the sample;
a variable integrated computational element (ICE) to receive a sample light and yield a readout sample light;
a detector to provide a signal from a readout sample light; and
a controller to provide an adjustment signal to the variable ICE.

10. The optical measurement system of claim 9 further comprising a feedback control loop to adjust the variable ICE.

11. The optical measurement system of claim 9 wherein the variable ICE comprises a layer of a dielectric material;
a transparent electrode adjacent to the layer of dielectric material;
a second electrode adjacent to the layer of dielectric material, opposite to the transparent electrode;
wherein the dielectric material is strained in the presence of an electromagnetic field.

12. The optical measurement system of claim 11, further comprising a hydrocarbon recovery system comprising an apparatus for deploying the variable ICE in a wellbore, the apparatus selected from the group consisting of a wireline, a slickline, a coiled tubing and a drillstring.

13. A method for measuring sample properties, the method comprising:
identifying a desired property of a sample to be measured;
applying an adjustment signal voltage to an integrated computational element (ICE) to alter the optical properties of the ICE;
providing an illumination light to a sample to yield a sample light;
interacting the sample light with the ICE; and
measuring a readout sample light from the ICE.

14. The method of claim 13 further comprising
obtaining a value for an unknown sample property;
measuring an environmental property with a sensor;
measuring the sample property for a calibration set; and
providing a adjustment signal to the ICE upon the measurement of the
environmental property and the measurement of the calibration set.

15. The method of claim 14 wherein wherein measuring the sample property for a calibration set comprises obtaining a quality value from the calibration measurements by obtaining a standard error of calibration.

16. The method of claim 13 wherein providing a adjustment signal to the ICE comprises providing a voltage difference between a first electrode and a second electrode having a dielectric layer of material in between the first electrode and the second electrode.

17. The method of claim 16 further wherein providing the voltage difference comprises determining the voltage difference according to a strain in the dielectric layer of material to compensate a change in a measured environmental property.

18. The method of claim 16 further wherein providing the voltage difference comprises determining the voltage difference according to a strain in the dielectric layer of material to improve a quality value from a calibration measurements.

19. The method of claim 13 wherein providing a adjustment signal to the ICE comprises providing a current flow between a first electrode and a second electrode having a dielectric layer of material in between the first electrode and the second electrode.

20. The method of claim 19 further wherein providing the current flow comprises determining the current flow according to a strain in a dielectric layer of material to compensate a change in a measured environmental property.

21. The method of claim 19 further wherein providing the current flow comprises determining the current flow according to a strain in the dielectric layer of material to improve a quality value from a calibration measurements.

22. The method of claim 13, further comprising:
deploying the ICE in a wellbore; and
measuring a property of a fluid within the wellbore utilizing the ICE.

* * * * *

UNITED STATES PATENT AND TRADEMARK OFFICE
CERTIFICATE OF CORRECTION

PATENT NO. : 9,683,932 B2
APPLICATION NO. : 14/904474
DATED : June 20, 2017
INVENTOR(S) : Michael T. Pelletier et al.

It is certified that error appears in the above-identified patent and that said Letters Patent is hereby corrected as shown below:

In Column 5, Line 40: replace "T" with --'i'--;

In Column 7, Line 50: replace "X" with --$\lambda$--;

In Column 7, Line 56: replace "$\lambda$" with --$\lambda_1$--;

In Column 8, Line 30: replace "T odd" with --'i' odd--;

In Column 8, Line 30: replace "T even" with --'j' even--.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*